(12) United States Patent
Beckman et al.

(10) Patent No.: US 6,638,749 B1
(45) Date of Patent: *Oct. 28, 2003

(54) CARBON DIOXIDE SOLUBLE SURFACTANT HAVING TWO FLUOROETHER $CO_2$-PHILIC TAIL GROUPS AND A HEAD GROUP

(75) Inventors: Eric J. Beckman, Edgewood, PA (US); Eliador J. Ghenciu, Pittsburgh, PA (US); Nathaniel T. Becker, Burlingame, CA (US); Landon M. Steele, Brisbane, CA (US); Alan J. Russell, Wexford, PA (US)

(73) Assignees: Genencor International, Inc., Palo Alto, CA (US); University of Pittsburgh, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/004,603

(22) Filed: Jan. 8, 1998

Related U.S. Application Data

(60) Division of application No. 08/747,474, filed on Nov. 12, 1996, which is a continuation-in-part of application No. 08/558,068, filed on Nov. 13, 1995, now abandoned.

(51) Int. Cl.$^7$ ............................. A23J 1/00; C07K 1/00; C12N 9/00; C12N 9/48; C12P 1/00
(52) U.S. Cl. ....................... 435/212; 435/41; 435/183; 530/422
(58) Field of Search ........................... 95/154; 435/112, 435/168, 41, 183, 212; 8/142; 510/291, 466; 530/422; 424/70.19, 70.21, 70.22, 70.24, 70.28; 514/975

(56) References Cited

U.S. PATENT DOCUMENTS 5,734,023 A * 3/1998 Nag et al. .................. 530/403

FOREIGN PATENT DOCUMENTS

| EP | 0 531 104 A2 | 3/1993 |
|---|---|---|
| WO | WO87/02697 | 5/1987 |
| WO | WO96/27704 | 9/1996 |

OTHER PUBLICATIONS

Adamsky et al., "Inverse emulsion polymerization of acrylamide in supercritical carbon dioxide," *Macromolecules*, vol. 27, No. 1, pp. 312–314 (1994).

Hoefling et al., "Microemulsions in near–critical and supercritical dioxide," *Chemical Abstracts*, vol. 115, No. 16, Abstract No. 167171 (1991) and *J. Phys. Chem.*, vol. 95, No. 19, pp. 7127–7129.

Hoeffling et al., "Design and synthesis of highly carbon dioxide–soluble surfactants and chelating agents," *Chemical Abstracts*, vol. 118, No. 26, Abstract No. 257005 (1993) and *Fluid Phase Equilib.*, vol. 83, pp. 203–212.

Hoefling et al., "The incorporation of a fluorinated ether functionality into a polymer or a surfactant to enhance carbon dioxide solubility," *Chemical Abstracts*, vol. 118, No. 26, Abstract No. 257738 (1993) and *J. Supercrit. Fluids*, vol. 5, No. 4, pp. 237–241 (1992).

Hoefling et al., "Effect of structure on the cloud–point curves of silicone–based amphiphiles in supercritical carbon dioxide," *Chemical Abstracts*, vol. 121, No. 10, Abstract No. 111961 (1994) and *J. Supercrit. Fluids*, vol. 6, No. 3, pp. 165–171 (1993).

Newman et al., "Phase behavior of fluoroether–functional amphiphiles in supercritical carbon dioxide," *Chemical Abstracts*, vol. 122, No. 2, Abstract No. 12529 and *J. Supercrit. Fluids*, vol. 6, No. 4, pp. 205–210 (1993).

Singley et al., "Phase behavior and emulsion formation of novel fluoroether amphiphiles in carbon dioxide," *Chemical Abstracts*, vol. 126, No. 19, Abstract No. 252680 (1997) and *Fluid Phase Equilib.*, vol. 128, No. 1–2, pp. 199–219.

* cited by examiner

*Primary Examiner*—David M. Naff
*Assistant Examiner*—Deborah K. Ware
(74) *Attorney, Agent, or Firm*—Genencor International, Inc.; University of Pittsburgh

(57) ABSTRACT

There is provided a process for the extraction of water soluble biomaterials such as enzymes or proteins into carbon dioxide utilizing certain carbon dioxide-soluble surfactants. Also provided are certain carbon dioxide-soluble surfactants useful in the extraction of proteins. The surfactants are selected from fluoroether sulfate, fluoroether-polyethylene glycol block copolymer, fluoroether-functional sorbitol, and fluoroether dithiocarbamate chelate.

8 Claims, 5 Drawing Sheets

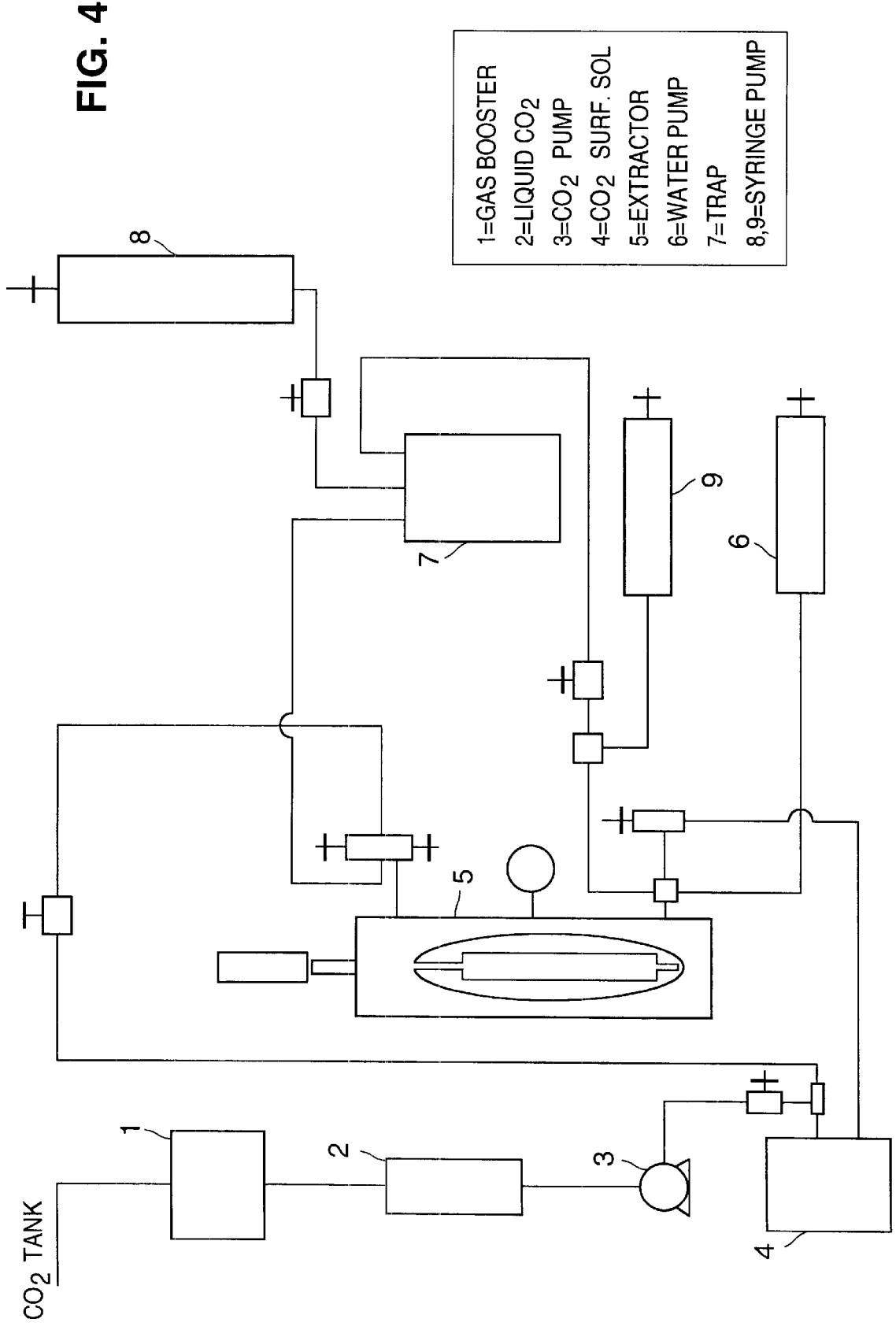

CARBON DIOXIDE SOLUBLE SURFACTANT HAVING TWO FLUOROETHER $CO_2$-PHILIC TAIL GROUPS AND A HEAD GROUP

CROSS-REFERENCE TO RELATED APPLICATIONS

This application is a divisional of U.S. application Ser. No. 08/747,474 filed Nov. 12, 1996, which is a continuation-in-part of U.S. application Ser. No. 08/558,068 filed Nov. 13, 1995, now abandoned, and which is incorporated herein by reference in its entirety.

FIELD OF THE INVENTION

This application relates to the extraction of water soluble biomaterials such as proteins and enzymes into carbon dioxide, using surfactants soluble in carbon dioxide. Furthermore, the present invention relates to certain novel carbon dioxide-soluble surfactants.

BACKGROUND OF THE INVENTION

As is well known, purification of proteins from cell broth is usually a multi-step process involving cell separation, concentration and fractionation by methods such as chromatography. From a process standpoint, particularly with regard to throughput, it would be advantageous to directly extract proteins from whole broth by means such as micellar liquid-liquid extraction, however, lack of selectivity and product recovery difficulties have until now precluded the use of such purification methods on a large scale. As described by Hatton, T. A. et al. in *Surfactant Based Separation Processes*, Scamehorn, J. F. and Harwell, J. H., eds., p. 5 (1989), surfactants can be employed to extract proteins from a buffer to an organic phase, generally through manipulation of the physiochemical properties of the aqueous phase such as pH, ionic strength, etc. So far the organics which have been found to be useful are hydrocarbons, which are toxic and flammable, and thus undesirable from a commercial perspective.

Reverse micelles have also been used to solubilize proteins of industrial relevance. In reverse micelles, or water-in-oil microemulsions, polar molecules such as water, salts and proteins can be solubilized by the polar groups of organic soluble surfactants. Aires-Barros, M. R. et al., *Biotech. Bioeng.* 38:1302 (1991), describes the separation and purification of two lipases using liquid-liquid extraction which was carried out in isooctane and utilized sodium di-2-ethylhexylsulfosuccinate as the surfactant. Dekker, M. et al., *Chem. Eng. J.* 33B:27 (1986), describe the recovery of α-amylase by liquid-liquid extraction into isooctane using trioctylmethylammonium chloride as the surfactant. Further, surfactant systems have been used to extract proteins from complex matrices, including fermentation broth and dried solids. (See Rahaman, R. S. et al., *Biotech. Progr.* 4:218 (1988); and Leser, M. E. et al., *Chimia* 44:270 (1990), respectively.)

It has been demonstrated that micellar systems allow not only extraction of proteins from aqueous solution, but also separation of certain protein mixtures. Goklen, K. E. et al., *Sep. Sci. Tech.* 22:831 (1987), show that separation of protein mixtures has been achieved through control of pH. Thus, proteins are separated by adjusting the pH of the micellar phase relative to the protein's isoelectric point(s). Salt concentration (which regulates water content, and thus micelle size) and the use of amphiphilic compounds which incorporate affinity ligands are another way to control separation. Work by Hatton et al. (supra) has shown that the affinity ligand approach yields a stronger interaction between the extracted protein and the micellar phase, and thus, allows protein solubilization over a wider range of pH and salt concentration.

While intriguing, micellar extraction of proteins cannot presently compete with other separation technologies owing to low overall protein recovery and difficulty in re-use of the organic phase, which is itself tied to the mechanism by which the protein is back-extracted. John, V. J. et al., *J. Supercrit. Fl.* 4:238 (1991), describe an approach to circumvent the back-extraction problem through the addition of a highly compressible organic component to the microemulsion. In this approach the formation of clathrate hydrates caused by the added organic removed water from the micelles and precipitated the protein. This technique, while successful on a small scale, does not entirely resolve the problem of protein recovery given that a let-down of the pressure permits resolubilization of both water and protein. Molecular sieves have been employed in conventional liquid emulsions for similar purposes. A final approach to addressing the back-extraction problem relates to increasing the salt concentration, or adding disrupting agents such as ethyl acetate or ethanol to dewater the reverse micelles, thus inducing protein precipitation from the emulsion. Such tactics may damage certain proteins, and none of these strategies address the overall problem of use of large volumes of an organic, solvent in contact with an aqueous phase. Clearly, the organic will contaminate the aqueous phase to some extent, which will require remediation prior to discharge.

One should be able to induce protein migration by varying the organic phase properties, as well as those of the aqueous phase. (See Hatton, T. A. et al., supra, for discussion of variables which induce protein migration.) As first shown by Smith, R. D. et al., *J. Phys. Chem.* 95:3253 (1991), variation of the pressure in a near- or supercritical fluid propane-based emulsion will indeed prompt proteins to migrate from the aqueous phase to the organic phase. Further, solubilization of a protein without a significant loss in activity in a propane-based emulsion allows extraction and recovery through pressure manipulation. (Ayala et al. (1992) *Biotechnology and Bioengineering* 39:806–814; Ayala et al. (1992) *Biotechnology* 10:1584–1588.)

Despite these favorable results, use of propane on a large scale is precluded by safety and environmental considerations. Indeed, use of most any organic solvent on a large scale could be unacceptable or very costly, owing to regulations regarding volatile organic chemical (VOC) emulsions, plus toxicity and safety issues.

In contrast to conventional organic solvents, carbon dioxide is inexpensive, occurs naturally in large quantities, is relatively non-toxic, is non-flammable and is not considered to be a VOC by federal authorities. In addition, carbon dioxide has a low critical temperature (~31° C.), allowing it to be used for extraction of thermally labile material. Consequently, carbon dioxide has been identified as an environmentally-benign organic solvent in such diverse areas as analytical chromatography, biocatalysis, polymerization and extraction of thermally-labile constituents from natural products. Because carbon dioxide is a gas under ambient conditions, reduction of the pressure to atmospheric in carbon dioxide-based solutions induces complete precipitation of solute, rendering solute concentration/recovery and solvent recycle operations somewhat easier than in conventional liquid systems. However, despite its inherent physical property advantages, carbon dioxide by itself is a relatively non-polar material, and thus will not solubilize highly polar and hydrophilic solutes.

In the late 1980's researchers at the University of Texas-Austin and Battelle's Northwest Laboratories investigated the use of surfactants to improve the solubility of polar solutes in non-polar supercritical fluids. Formation of reverse micelles in supercritical alkanes did indeed dramatically increase the supercritical fluid's ability to solubilize amino acids, water-soluble polymers, proteins and metal-containing compounds. Gale, R. W.; Fulton, J. L.; Smith, R. D. (1987) *J. Am. Chem. Soc.* 109:920 and Hoefeling, T. A. et al. (1991) *J. Phys. Chem.* 95:7127. However, extension of the use of surfactants to environmentally-benign carbon dioxide was blocked by the experimental observation that commercially available ionic amphiphiles, while highly soluble in alkanes such as ethane and propane, exhibit poor to negligible solubility in carbon dioxide at moderate pressures (10–500 bar). These findings were discussed in Consani, K. A., *J. Supercrit.* Fl. 3:51 (1990). Thus, in carbon dioxide/water mixtures, these conventional hydrocarbon surfactants tend to partition to the aqueous phase, forming normal micelles. Nonionic ethoxylated alcohols as well as other surfactants, while somewhat soluble in carbon dioxide, exhibit poor water absorption capability, making these unacceptable as surfactants to use with carbon dioxide for solubilizing biomolecules such as proteins. The results of the work described in this reference are summarized in Table 1 in the Experimental section herein.

To address the problem of the insolubility of standard surfactants in carbon dioxide the applicants have investigated the rational design and synthesis of carbon dioxide-soluble amphiphiles. Unlike conventional compounds of this nature, in which an alkane tail (or tails) is typically covalently bonded to the head group, the surfactants useful in the present invention possess a hydrophobic tail comprised of functional groups designed to interact favorably, in a thermodynamic sense, with carbon dioxide (these are subsequently referred to as carbon dioxide-philic or $CO_2$-philic tail groups).

An extraction process using a surfactant which allows the use of carbon dioxide as the organic solvent would have many advantages. Water soluble biomaterials such as enzymes and other proteins could be extracted directly from the whole or diluted fermentation broth while leaving cells, debris and other impurities behind, thereby reducing the steps in the recovery train. The excellent mass transfer properties of the high pressure carbon dioxide allow for rapid extraction kinetics. When the polar compound to be extracted by the present invention is a protease (subtilisin), it is contemplated that the low water environment reduces hydrolytic autolysis which in turn enhances enzyme stability. Isothermal decompression of the carbon dioxide provides a simple means of back-extracting the enzyme in a highly purified form. The protein can then be separated from the surfactant by appropriate buffer use to reduce interactions. The surfactant(s) will be only negligibly soluble in aqueous buffer. A continuous process utilizing high pressure carbon dioxide would reduce the demand for raw materials and energy.

The present invention, therefore, relates to certain carbon dioxide-soluble surfactants and the use of such in extracting water soluble biomaterials such as proteins into carbon dioxide. While the recovery of the current process has not been fully optimized, the present invention demonstrates the first extraction of protein compounds utilizing $CO_2$.

SUMMARY OF THE INVENTION

According to the present invention, there are provided amphiphilic compounds comprising:

a) one or more $CO_2$-philic tail group(s) selected from the group consisting of a flouroether, oligomers of propylene-oxide, halogen substituted alkyl (C1–C12) and a siloxane or a copolymer thereof; and b) one or more head group(s) that interacts with a water soluble biomaterial through cationic, anionic, non-ionic, amphoteric, metal chelate, hydrophobic interaction or affinity interactions.

The amphiphilic compounds of this invention are particularly useful for the extraction of water soluble biomaterials, provided the amphiphilic compounds are soluble in $CO_2$.

In a method embodiment of the present invention there is provided a method for the extraction of water soluble biomaterial (such as protein or enzyme) from a fluid, which method comprises dissolving at least one carbon dioxide-soluble surfactant in carbon dioxide to form a carbon dioxide/surfactant mixture and adding to such carbon dioxide/surfactant mixture an aqueous solution comprising a water soluble biomaterial under appropriate conditions to allow the water soluble biomaterial to be extracted into the carbon dioxide.

Although a preferred embodiment of this process comprises dissolving the surfactant in the $CO_2$ and then adding the aqueous solution containing the biomaterial to be extracted, those skilled in the art would readily recognize that the surfactant could be added to the $CO_2$ before or after the aqueous solution has been contacted with the $CO_2$. In a preferred process embodiment the aqueous solution is a whole fermentation broth which has been filtered to remove cells and/or cellular debris, though use with unfiltered broth is also envisaged.

In a preferred process embodiment the surfactant is an amphiphilic compound comprising:

a) one or more $CO_2$-philic tail group(s) selected from the group consisting of a fluoroether, oligomers of propylene-oxide, halogen substituted alkyl (C1–C12) and a siloxane or a copolymer thereof; and b) one or more head group(s) that interacts with a water soluble biomaterial through one or more cationic, anionic, non-ionic, amphoteric, metal chelate, hydrophobic interaction or affinity interactions.

BRIEF DESCRIPTION OF THE DRAWINGS

FIG. 4 describes an apparatus useful for protein extractions as exemplified herein.

DETAILED DESCRIPTION OF THE INVENTION

Figure 1A:
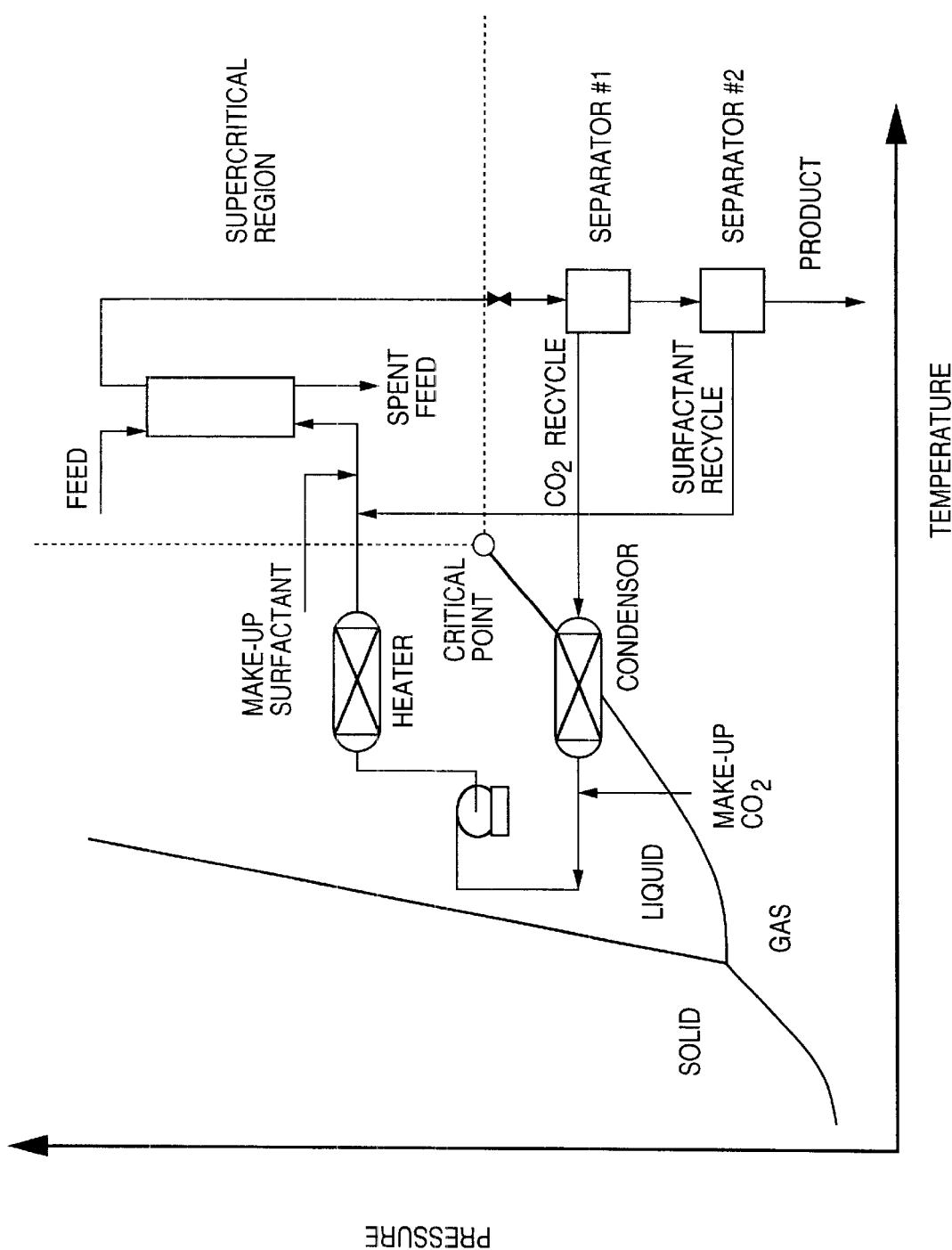
FIG. 1A is a schematic for tracking a fermentation broth through a continuous extraction process into supercritical carbon dioxide utilizing the present invention.

Surprisingly, it has been found that the utilization of the amphiphilic compounds described in the present invention allow for the extraction of water soluble biomaterials such as proteinaceous and enzymatically active materials into carbon dioxide. These amphiphilic compounds have one or more head group(s) with one or more tail group(s) (as defined above) and are soluble in carbon dioxide. The unique property of these compounds, solubility in carbon dioxide, is primarily due to the nature of the tail group employed. Specifically, the incorporation of a $CO_2$-philic tail group with a known or typical head group imparts this favorable characteristic on the compounds.

As used herein, the head group refers to the portion of the molecule which interacts with the protein. The head group can fall into one of two functional groups, either hydrophilic or protein-associating. These functional groups are well known in the art and the protein interactions they exhibit have been well studied. (See *Protein Purification Methods, A Practical Approach*, edited by E. L. V. Harris and S. Angal (1989).) The hydrophilic functionality can be nonionic such as ethylene oxide polymers, ethoxylates (such as polyethylene glycol), ethylene oxide-propylene oxide copolymers, amine oxides, alkanolamides, glycols, glycerols, monoglycerides, sugars (such as glucose or sucrose), polysaccharides, proteins, peptides, sorbitan derivatives, derivatives of betaine, lanolin, lignin, thio-and mercapto derivatives; or anionic such as sulfates, sulfonates, sulfosuccinates, phosphates, acrylic acid, organic acids; or cationic such as quaternary amines; or zwitterionic such as betines. The protein-associating functionality can associate via an ion-exchange mechanism using, for example, a deprotonated ionic functionality such as sulfate, sulfonate, carboxylate, quaternary amine and diethylaminoethyl (DEAE), which carries a net charge opposite to that of the protein at the intended pH of extraction; or via hydrophobic interactions, using groups such as phenyl or short alkyl chains typically utilized in hydrophobic interaction chromatography; or via a mechanism analogous to immobilized metal affinity chromatography (IMAC), using metal chelates that form complexes with the histidine groups on proteins; or via affinity interaction, using groups such as biotin or phenyl boronate, which form highly biospecific complexes with particular complementary proteins via biological relationships such as substrate, inhibitor, coenzyme, receptor, antibody, or subunit associates. Also falling into the category of affinity interactions would be the non-natural pseudo-affinities such as dye groups that interact with proteins.

As used herein, the tail group refers to the portion of the surfactant molecule which is soluble in liquid or supercritical carbon dioxide. The $CO_2$-philic tail can be a number of alternative chemical classes. The preferred $CO_2$-philic tails include fluoroethers, silicone glycols and siloxanes, as shown below. The solubility of these tails in carbon dioxide allows protein to be extracted into the carbon dioxide. The solubility in carbon dioxide of certain of these surfactants is shown in Table 1 in the Experimental section herein.

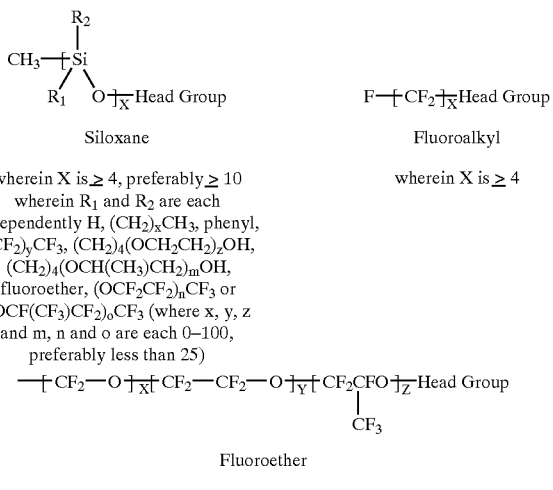

Siloxane wherein X is ≥ 4, preferably ≥ 10
wherein $R_1$ and $R_2$ are each independently H, $(CH_2)_xCH_3$, phenyl, $(CF_2)_yCF_3$, $(CH_2)_4(OCH_2CH_2)_zOH$, $(CH_2)_4(OCH(CH_3)CH_2)_mOH$, fluoroether, $(OCF_2CF_2)_nCF_3$ or $(OCF(CF_3)CF_2)_oCF_3$ (where x, y, z and m, n and o are each 0–100, preferably less than 25)

Fluoroalkyl wherein X is ≥ 4

Fluoroether wherein the sum of X, Y and Z is ≥ 4

Utilizing the teachings of the present invention, one can design a surfactant soluble in carbon dioxide, which surfactant is specifically targeted to a particular protein or proteinaceous material to be extracted. The surfactant is designed by choosing a head group which specifically interacts with the protein of interest and a $CO_2$-philic tail group which will render it soluble in $CO_2$. In this way a very specific extraction can be performed by carefully selecting a head group which has a strong affinity or interaction with the water soluble biomaterial (protein or proteinaceous material or a portion of the protein or proteinaceous material) to be extracted. The affinity of a given head group for a particular protein is information either available to the skilled artisan or readily ascertainable by the artisan (*Protein Purification Principles, High Resolution Methods, and Applications*, Jan-Christen Jansen and Lars Ryden, Eds., VCH Publishers, 1989, New York).

Water soluble biomaterial can be any material made biologically and having a solubility in water of greater than 1 g/L, including proteinaceous material such as enzyme, antibody, peptide, amino acid, polysaccharide, sugar, peptide hormone, transport molecule or any material resembling a protein.

As used herein, a supercritical fluid is a dense fluid at a temperature and pressure at or above the critical point. Supercritical fluids have physical properties between those of liquids and gases. Near the critical point, small changes in pressure or temperature cause very large changes in solvent density, and hence in dissolving power. A subcritical fluid is a gas or liquid with either a temperature or pressure that is below its critical point (Kirk-Othmer Encyclopedia, 3rd Ed., 872–893, 1989).

High pressure carbon dioxide may be either supercritical or subcritical, with the critical point defined as the highest pressure and temperature at which distinct liquid and gas phases can co-exist. The critical point of carbon dioxide is 31.06° C. and 73.83 bar (1068.9 psi).

The surfactants of the present invention can be used alone or in conjunction with any other surfactant or cosurfactant useful for the extraction of proteinaceous material. In the process embodiments of the present invention, the surfactants are soluble in the carbon dioxide which is either subcritical or supercritical. The extraction process using carbon dioxide and the surfactants defined herein is generally similar to a liquid-liquid process as known to those skilled in the art. The examples provided herein show a batch extraction process. These examples demonstrate the feasibility of a $CO_2$ extraction with activity retention of the biomaterial so extracted. However, one skilled in the art will readily recognize optimizations of the described process, including a continuous process with potential recycling of the carbon dioxide and/or surfactant.

As used herein, "appropriate conditions" are determined on a case-by-case basis as readily understood by the skilled artisan, taking into consideration all elements of the system, the pH, ionic strength, temperature or pressure, all of which control "phase behavior." Additionally, the artisan considers the protein interaction with the head group. Thus, considering all these factors, appropriate conditions are those encouraging interactions of the protein and head group of surfactants.

Figure 1B:
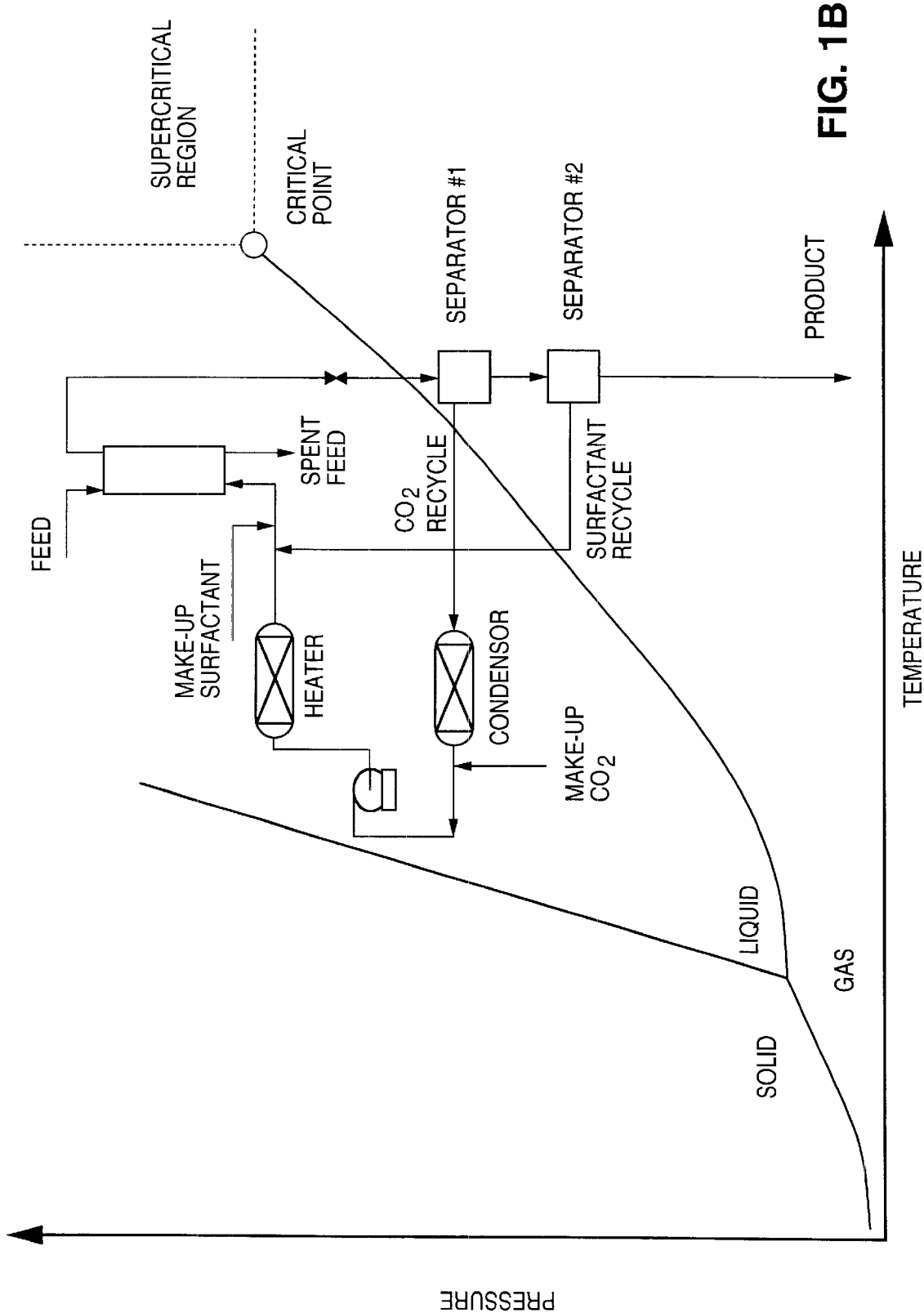
FIG. 1B is a schematic for tracking a fermentation broth through a continuous extraction process into subcritical carbon dioxide utilizing the present invention.

The schematic shown in FIG. 1 describes a continuous recovery of protein from any fluid containing proteinaceous material. Generally, the feedstock (or feed broth) is raised to the pressure at which the extraction will occur. The feedstock is then sent to a countercurrent extraction column where it is contacted with high pressure carbon dioxide containing the dissolved surfactant at the appropriate concentration. The products from the extraction column consist of a spent broth stream and a stream with a carbon dioxide continuous phase containing the surfactant, the extracted product and extracted water or buffer. The spent broth can either be recycled into the feedstream if the extraction is incomplete or it can be discarded. A rapid decompression step should be sufficient to inactivate any live cells, thereby allowing for inexpensive disposal and possible use of the cell mass for composting, fertilizer or any number of other uses. The high pressure $CO_2$ phase stream is then passed through a settler to remove any entrained liquid and then decompressed, temperature adjusted, or both to change the phase behavior of the mixture and lower the solubility of the surfactant, water and product in the $CO_2$ so that the product and surfactant can be separated from the $CO_2$. This is an effective back-extraction method, and requires only small changes in temperature or pressure when the $CO_2$ is in the supercritical regime. Therefore, this back-extraction has the advantage of being rapid, energy efficient and complete. It also allows for virtually complete recycle of the $CO_2$, which must be brought back to its original pressure and temperature conditions before recycle. Any loss would be compensated for with $CO_2$ makeup.

Similarly, the recovered product, including the surfactant and water that drop out of the $CO_2$, would decompress at an appropriate rate and temperature to prevent.denaturation. Buffer can be added at this point to formulate the product or to break any surfactant/protein interaction. Elution of the protein from the surfactant will depend on the mechanism of association. For example, ionic surfactants may require addition of salts to displace bound protein. Since the novel surfactants used are either minimally water soluble or completely insoluble, the aqueous product solution and the surfactants could be easily separated by decanting or other physical means known to those skilled in the art. The surfactant can then be further treated if necessary and recycled, using surfactant makeup to compensate for any loss. The recovered product is then ready for any necessary further downstream processing such as further purification, concentration, filtration or formulation.

The following Materials and Methods, and Experimental sections further describe the present invention.

Materials and Methods

Figure 2:
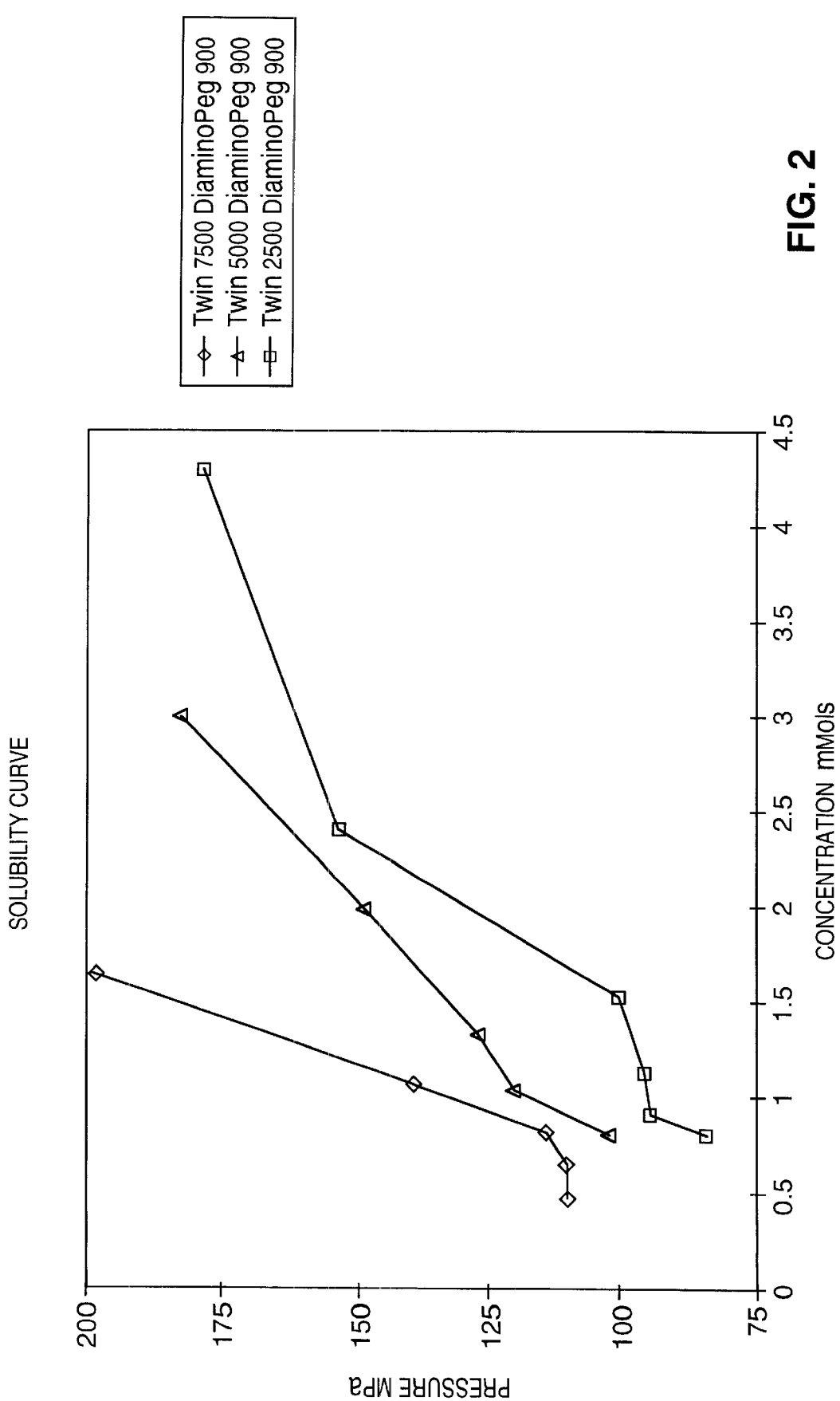
FIG. 2 is a plot of the solubility under pressure (phase behavior) of three twin-tailed fluoroether-polyethylene glycol block copolymers with different tail lengths in carbon dioxide. Their synthesis is described in Example 1.

The extraction experiments detailed herein were conducted in a pressure cell apparatus as shown in FIG. 4. The phase behavior or solubility of the novel surfactants in carbon dioxide under pressure was measured in a high pressure, variable volume view cell. The surfactant was loaded into the top of the quartz cylinder encased in a stainless steel window cell. The cell was sealed and $CO_2$ was injected via a Ruska syringe pump. The pressure in the system was regulated by movement of the floating piston, adjusted by injecting or withdrawing silicone oil. Seals located on the piston and the top of the quartz cylinder prevent mixing of the sample and the silicone oil. Phase transitions were observed by increasing pressure until a single-phase existed, then slowly lowering pressure until the system appeared cloudy. Initial work showed that each of the model surfactants were soluble in carbon dioxide to some degree at reasonable pressures (FIG. 2). Further solubility data for specific surfactants described herein are provided below in Table 1, as compared to the solubility of surfactants of the prior art (Consani, K. A., *J. Supercrit*. Fl. 3:51 (1990)).

Figure 3:
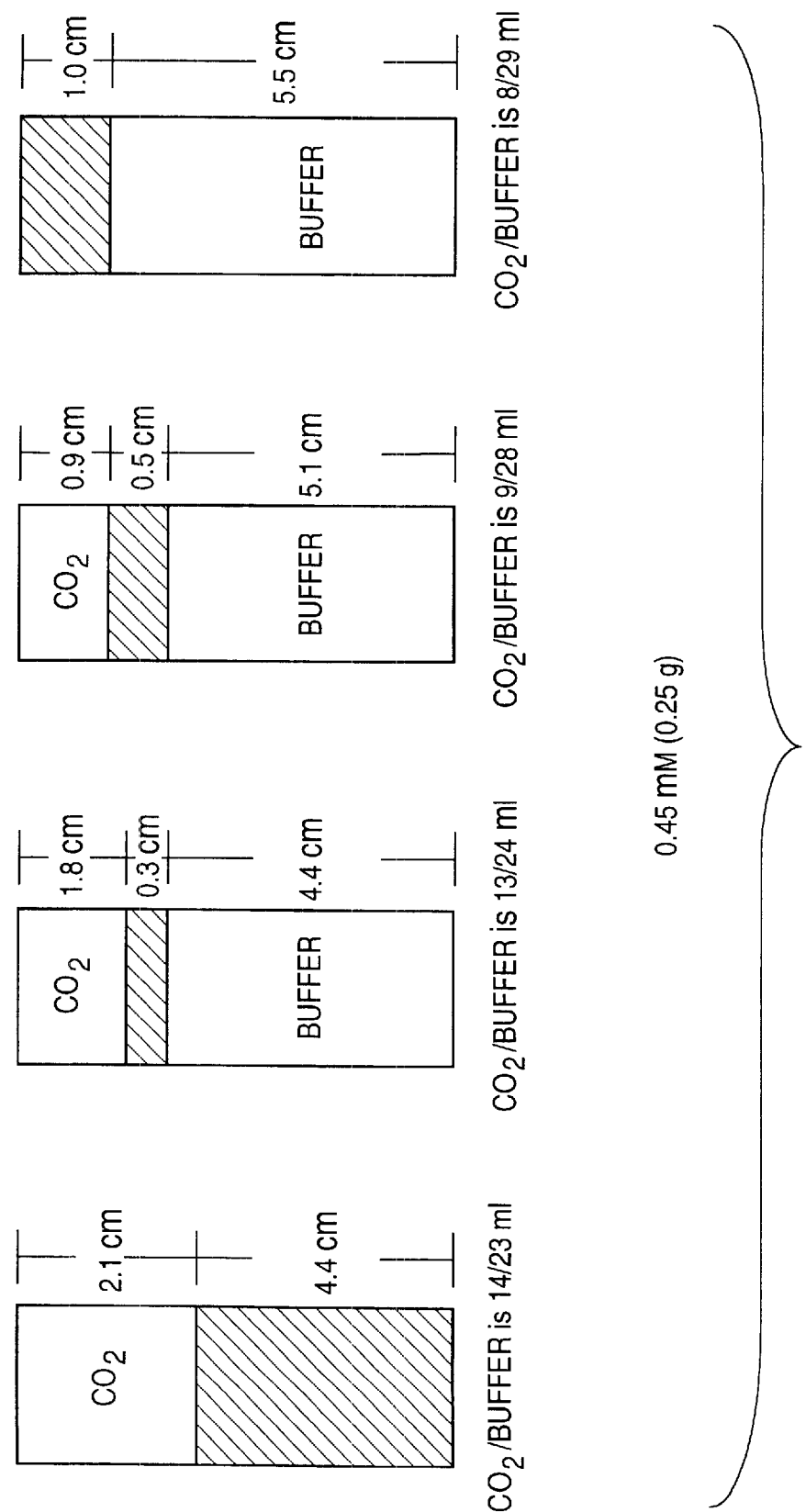
FIG. 3 shows the various states of a three-phase systems in relation to the ratio of carbon dioxide to buffer.

To determine the emulsion formation characteristics for Twin Tail Sodium Sulfate (FSH) in a $CO_2$/buffer mixture, a known quantity of the surfactant and phosphate buffer (pH=7.4, ionic strength=0.01 M) were loaded into the view cell, which was then sealed and brought to the required temperature. A known quantity of carbon dioxide was added via the syringe pump and the contents of the cell mixed by rocking the cell. The phase behavior was then observed at various pressures, allowing time between each measurement to allow the contents of the cell to settle. Following a pressure scan, either water or $CO_2$ was injected, and the pressure scan repeated at the new water:$CO_2$ ratio. Use of a cathetometer allowed calculation of phase volumes. The amount of emulsion formed, the layer in which the emulsion is formed and the presence of an emulsion third phase is dependent on the ratio of carbon dioxide to buffer. This is shown in FIG. 3.

The following examples are representative and not intended to be limiting. One skilled in the art could choose other head and tail group combinations based on the teachings provided herein and could further optimize the extraction process.

Experimental

EXAMPLE 1

Synthesis of Model Surfactants

A. Fluoroether Head Groups

1. Fluoroether Sulfates

Fluoroether sulfate surfactants useful in the present invention were generated via formation of a hydroxyethyl ester of the fluoroether carboxylic acid, followed by reaction of the terminal hydroxy group with chlorosulfonic acid. The first step of this procedure was the transformation of the fluoroether acid to the acid chloride.

Typically, 50 g of the 2500 molecular weight fluoroether acid (0.02 mole, Krytox Functional Fluid FSL, DuPont) were dissolved in an equal amount of previously dried perfluoromethyl cyclohexane in a three-neck flask equipped with nitrogen inlet and dry-ice coldfinger. Following dissolution of the fluoroether, 1.46 g (0.02 mole) dimethyl formamide were added and the temperature brought to 70° C. while stirring. At this point, 2.38 g of thionyl chloride were added and the mixture allowed to react for 2 hours. An additional 3.57 g thionyl chloride (0.03 mole) were then added and the mixture allowed to react for an additional 5 hours. At this point, the solvent and excess reactants were removed under vacuum at 80° C. and the product analyzed. Characterization of the product by FT-IR shows a shift of the carbonyl peak from 1776 $cm^{-1}$ to 1807 $cm^{-1}$; $^1$H NMR revealed a disappearance of the peak for the acid proton at 9.16 ppm; $^{13}$C NMR showed a shift of the carbonyl carbon peak from 163.5 to 161.5 ppm.

The hydroxyethyl ester of the fluoroether acid was prepared via reaction of the acid chloride with an excess of ethylene glycol. Here, 25 g of the fluoroether acid chloride (0.01 mole) were dissolved in 1,1,2 trifluorotrichloroethane under nitrogen. Subsequently, 1.24 g ethylene glycol (0.02 mmole) in 10 ml THF were added at room temperature. An excess of a cross-linked, dimethylaminopyridine-functional polystyrene resin (PolyDmap) was added to scavenge HCl. After 24 hours, the PolyDmap was removed by filtration and the solvents removed under vacuum. The product was washed several times with acetone to remove excess ethylene glycol and then vacuum dried for 24 hours. (FT-IR, —COOR, 1790 $cm^{-1}$, $CH_2OH$, 3400 $cm^{-1}$; $^1$H NMR —$OCH_2$—C, 4.29, 2H; —C—$CH_2$—O, 3.69, 2H; —OH, 5.02 ppm, 1H.)

The sulfonate group was then formed via the reaction between the fluoroether hydroxyethyl ester and chlorosulfonic acid. Typically, 25 g of the hydroxyethyl ester (0.01 mole) were dissolved in 30 ml of 1,1,2 trifluorotrichloroethane under a nitrogen atmosphere. While stirring vigorously, 1.17 g chlorosulfonic acid (0.01 mole) were added. During the reaction, HCl bubbles were observed to form and were swept out of the reaction flask by flowing nitrogen. After 1.5 hours, the solvent and residual HCl were removed under vacuum at 50° C. $^1$H NMR showed the appearance of the sulfonic acid proton (10.59 ppm, 1 H), the disappearance of the hydroxy proton at 5.02 and a shift of the methylene protons (—C(O)$OCH_2$, 4.50 ppm, 2H; —$CH_2OSO_3$, 4.58 ppm, 2H). Finally, the sulfonic acid was neutralized via reaction with an excess of sodium trimethylsilanoate (1.0 M in THF). The product was washed several times with THF to remove residual reactants.

2. Fluoroether-Polyethylene Glycol Block Copolymers

Fluoroether-polyethylene glycol diblock surfactants useful in the present invention were synthesized via the transformation of the fluoroether acid to the acid chloride, followed by a single-phase reaction with an excess of polyethylene glycol (PEG). Typically, the fluoroether acid chloride was prepared as described above; 10 grams (4 mmole) were added to a $C_2Cl_3F_3$/THF mixture (4:1 volume ratio). A 5 molar excess of the particular PEG was then dissolved in a similar $C_2Cl_3F_3$/THF mixture (3:2 volume ratio). The PEG/$C_2Cl_3F_3$/THF mixture was heated to 35° C. under a nitrogen blanket and the acid chloride/$C_2Cl_3F_3$/THF mixture was added slowly over a two hour period while mixing. As before, PolyDmap was added to scavenge HCl. Once acid chloride addition was complete, the single-phase solution was allowed to mix for 24 hours. The PolyDmap was removed by filtration, the solvents were removed under vacuum and the excess PEG was decanted off. The resulting viscous product was then washed with water and vacuum dried over $P_2O_5$ at 50° C. for 24 hours. Characterization by FT-IR and 1H NMR showed essentially complete conversion (Perfluoroether—COOH, 1776 $cm^{-1}$, perfluoroether— COCl, 1809 $cm^{-1}$, perfluoroether C(O)-O-PEG (200, 600, 900 and 1500), 1784 $cm^{-1}$, —OH, 3400 $cm^{-1}$).

Fluoroether-alkyl ether-fluoroether triblock surfactants were prepared similarly to the diblock materials, although a 2:1 molar ratio of fluoroether acid chloride:polyethylene glycol was employed.

3. Fluoroether-Functional Sorbitols

Fluoroether-functional sorbitols useful in the present invention were synthesized as follows. Typically, 0.37 g sorbitol (4 mmole, Aldrich, vacuum dried at 80° C. for 48 hours) were dissolved in 25 ml of previously dried cyclopentanone at 80° C. Subsequently, 10 g (4 mmole) of the fluoroether acid chloride (synthesis described above) were dissolved in a large excess of 1,1,2 trichlorotrifluoroethane and added slowly to the sorbitol solution. PolyDmap was added to scavenge HCl. The resulting single-phase solution was allowed to react for 24 hours. Following removal of the PolyDmap and the solvent, the product was washed several times with ether to remove residual cyclohexanone. The product was then redissolved in 1,1,2 trifluorotrichloroethane, filtered to remove any unreacted sorbitol, then dried under vacuum. Characterization showed the formation of the sorbitol ester (FT-IR, shift of carbonyl peak from 1809 $cm^{-1}$ (acid chloride) to fluoroether ester (1789 $cm^{-1}$)), plus appearance of strong hydroxy stretching at 3400 $cm^{-1}$; by adjusting the molar ratio of fluoroether acid chloride to sorbitol, single-, twin- and triple-tailed amphiphiles have been produced.

4. Synthesis of Fluoroether Dithiocarbamate Chelate

The first step utilizes the synthesis of dithiocarbamate functionalized amine, using a procedure similar to that outlined by Sucre and Jennings ((1980) "Lithium Di (Trifluoroethyl) Dithiocarbamate: An Alternative Reagent for the Preparation of Di (Trifluoroethyl) Dithiocarbamate Metal Chelates," *Analytical Letters* 13(A6):497–501). The second step in the synthesis of these surfactants involves the formation of an amide linkage with the acid chloride functionalized fluoroether to form the dithiocarbamate functionalized fluoroether.

In a typical synthesis, 1.76 ml (20 mmoles) of N-methylethylenediamine (Aldrich) were dissolved in 25 ml of anhydrous diethylether. While keeping the contents under a blanket of nitrogen, the reaction flask was cooled to −70° C. using an acetone-dry ice bath. Stirring was started and 12.5 ml of a 1.6 M solution of butyl lithium (20 mmoles) in hexane were added to the solution dropwise over a period of 10 minutes. After one hour under the same conditions, 1.2 ml (20 mmoles) of carbon disulfide were added to the solution.: Stirring at −70° C. was continued for 30 more minutes and then the temperature was allowed to slowly rise to 0° C. where it was kept for 30 more minutes before it was allowed to rise to room temperature. The solvents and unreacted starting material were removed under vacuum at 80° C. The $^{13}$C NMR spectrum of the product showed the distinct —$CS_2H$ peak at 210 ppm and two peaks corresponding to the two carbons designated at 55 and 70 ppm, respectively. A 1.5 molar equivalent of this product was added to fluoroether acid chloride dissolved in a 4:1 mixture of 1,1,2 trichlorotrifluoroethane:acetone with PolyDmap. The reaction was allowed to proceed for a period of 24 hours at 40° C. Filtration was used to remove PolyDmap. 1,1,2 trichlorotrifluoroethane and acetone were removed by heating to 50° C. under vacuum. The product was then washed with acetone to remove the unreacted portion of the diamine.

The product was identified by disappearance of the acid chloride peak at 1808 $cm^{-1}$ and appearance of the amide peak at 1714 $cm^{-1}$ on the FT-IR spectrum. The $^{13}$C NMR spectrum of the product showed the distinct —$CS_2H$ peak at 215 ppm and two peaks corresponding to the two carbons designated at 50 and 70 ppm, respectively.

The copper chelate was prepared from the chelating agent by dissolving an amount of the chelating agent in freon 113, then adding this solution to a ten-fold excess of copper as aqueous copper sulfate. By mixing the organic/and aqueous solutions in a 2:8 v/v ratio, an emulsion formed in the organic phase, allowing good contact between the copper sulfate solution and the chelating agent. Subsequent UV analysis of the chelate confirms the presence of copper (which can also be seen by a visible color change).

Following the procedures outlined above in Example 1, various surfactants useful in the present invention were made. The $CO_2$-solubility of these surfactants was determined as detailed above in the Material and Methods section. The solubility data for surfactants useful in the present invention, particularly as compared to those of the prior art, are provided in Table 1.

surfactants made as per Example 1 and listed in Table 2 were loaded into the saturation cell (4), a simple, high pressure chamber (25 cm3) constructed at the University of Pittsburgh, which can be operated at pressures to 7500 psi. Subsequently, a solution of protein (subtilisin Carlsberg, Sigma Chemical Co.) in phosphate buffer (ionic strength= 0.01 M, pH=7.4 unless otherwise noted) was loaded into the extraction cell (5), a 35 cm3 vessel with aligned sapphire windows and equipped with a mechanical stirrer (modified Parr stirring unit). The buffer solution initially filled the extraction cell (usable pressure range up to 3500 psi). To begin the extraction, the saturation vessel was pressurized to the operating pressure (above the cloud point of the surfactant) using a Haskell gas booster (1) and supercritical grade carbon dioxide (Airco Specialty Gases). The valve to the extraction cell was opened slowly, and a manual syringe pump (9) was used to move the $CO_2$/surfactant solution to the extraction cell, while at the same time the other manual syringe pump (6) withdrew excess buffer. This charges the

TABLE 1

| | Solubility |
|---|---|
| Surfactants of Present Invention | |
| *Nonionics* | |
| Single tail fluoroether sorbitol, 2500 MW tail | 10 mM at 230 bar (33° C.) |
| Single tail fluoroether sorbitol, 5000 MW tail | 4 mM at 230 bar |
| Single tail fluoroether sorbitol, 7500 MW tail | 2 mM at 230 bar |
| Twin tail fluoroether sorbitol, 2500 MW tail | 6 mM at 230 bar |
| Twin tail fluoroether sorbitol, 5000 MW tail | 2.5 mM at 230 bar |
| Twin tail fluoroether sorbitol, 7500 MW tail | 1.5 mM at 230 bar |
| Triple tail fluoroether sorbitol, 2500 MW tail | 1.5 mM at 230 bar |
| *Anionics* | |
| Single tail fluoroether sulfate (sodium salt), 2500 MW tail | 1 mM at 230 bar (25° C.) |
| Twin tail fluoroether sulfate (sodium salt), 2500 MW tail | 2.5 mM at 230 bar |
| Single tail fluoroether sulfate (sodium salt), 7500 MW tail | 2 mM at 230 bar |
| Twin tail fluoroether sulfate (sodium salt), 7500 MW tail | 2 mM at 230 bar |
| Fluoroether carboxylate (sodium salt), 2500 MW | infinitely miscible at 230 bar (40° C.) |
| Fluoroether carboxylate (ammonium salt), 2500 MW | infinitely miscible at 230 bar |
| Fluoroether carboxylate (potassium salt), 2500 MW | 6.5 mM at 230 bar |
| Prior Art Surfactants | |
| *Anionics* | |
| Alkyl sulfonate ($C_6$, sodium salt, Fluka) | insoluble to 388 bar (50° C.) |
| Alkyl sulfonate (cocoyl, sodium salt, GAF (Igepon AC-78)) | insoluble to 388 bar |
| Alkyl sulfonate (Niacet, NAS 08) | insoluble to 585 bar |
| *Nonionics* | |
| PEG 400 monolaurate (Chem Services) | nearly miscible at 377 bar |
| PEG 600 monolaurate (Chem Services) | partly soluble at 377 bar |
| Sorbitan trioleate (Fluka, Span 80) | slightly soluble at 377 bar |
| Sorbitan monostearate (Fluka, Span 60) | slightly soluble at 377 bar |
| *Cationics* | |
| Tetradecyl trimethyl ammonium bromide (Fluka) | insoluble to 388 bar |
| Dimethyl dicoco ammonium chloride (Akzo Arquad 2C075) | slightly soluble at 487 bar |

EXAMPLE 2

Extraction of Protein into Carbon Dioxide

The following extraction process example is provided to demonstrate a specific process whereby applicants detail a batch extraction process useful for the recovery of water soluble biomaterials using $CO_2$-soluble surfactants described herein. Further optimization of the process is contemplated.

Protein extractions into carbon dioxide were initially performed using the apparatus shown in FIG. 4. First, the extraction cell with a homogeneous surfactant/$CO_2$ mixture without loss in pressure, and thus premature precipitation. After injecting the $CO_2$/surfactant mixture, both the buffer syringe pump and the saturation cell were isolated from the extraction cell. Finally, the collection cell was charged with carbon dioxide to the operating pressure.

The stirrer was started (400 rpm) in the extractor and the mixture allowed to stir for 5 minutes, after which the stirrer was shut down and the system allowed to settle for several minutes. The formation of the emulsion in the carbon dioxide was easily viewed through the sapphire windows of the extraction cell. After allowing the system to settle to equilibrium, a portion of the emulsion was moved to the collection cell (7) by re-injecting additional buffer using the high pressure syringe pump (6), and simultaneously withdrawing $CO_2$ using syringe pump (8). The volume of emulsion displaced was calculated from the distance which the emulsion/buffer interface had moved during removal of the emulsion phase.

Thus, a major portion of the emulsion was removed at constant pressure, without significantly disturbing the phase behavior of the system.

Following collection of the emulsion phase, the collection cell was valved off and slowly depressurized through the back pressure regulator. Aqueous phase present in the collection cell was removed and volume recorded. The residual surfactant in the vessel was washed with buffer; the washings were added to the other aqueous material collected. The collection vessel was then flushed with perfluorinated N-methyl morpholine (3M) to recover the surfactant.

The amount of subtilisin present in the aqueous buffer in the collection vessel was measured using the modified Lowry procedure (Sigma total protein kit No. 690; Perkin-Elmer Lambda II UV spectrometer). In addition, the activity of the enzyme recovered was assayed using the initial rate of decomposition of the substrate N-succinyl Ala-Ala-Pro-Phe p-Nitroanilide (Sigma). In this assay the amount of active enzyme in the sample was determined by measuring the rate of reaction of the peptide at a given substrate concentration by following the growth of the product peak at 410 nm, subtracting the rate of hydrolysis of the blank (no enzyme), then multiplying by a conversion factor for subtilisin.

Some early results, shown in Table 2, demonstrated that subtilisin was extracted into carbon dioxide while retaining activity. From the data, one can see that the subtilisin as received was only partially active enzyme. Further, the ratio of enzyme by the total protein kit (TPK) to that measured by the assay in the extracted material is lower than that for the starting material. Thus, we have either extracted preferentially the non-active components of the original subtilisin powder, or partially deactivated the enzyme through our extraction procedure. The results in Table 2 show that the surfactants we have employed are active in forming an emulsion at relatively low concentrations, less than 1 mM in carbon dioxide. As such, the ratio of surfactant molecules to protein molecules (S/P) in the extracted sample is relatively efficient (200 and below). As would be expected, the most efficient run (smallest surfactant to protein ratio) was Run No. 6, where the anionic sulfate (twin tailed fluoroether sulfate, 7500 MW tails) was employed under pH conditions (pH=5.1). At this pH the protein may be expected to be positively charged. In Run No. 5, the protein was recovered at 9.6%, with 5.6% recovery of active protein.

TABLE 2

| Run No. | Buffer/$CO_2$ (ml/ml)[a] | Pressure (psi) | Surfactant (mM) in $CO_2$[c] | initial protein[e] (mg) | initial active enzyme[f] (mg) | recovered protein[e] (mg) | recovered active enzyme[f] (mg) | S/P[g] |
|---|---|---|---|---|---|---|---|---|
| 1. | 28/8 | 2000 | 0.29 | 17.7 | 7.2 | 0.49 | 0.12 | 138 |
| 2. | 28/8 | 2200 | 0.34 | 17.9 | 7.3 | 0.73 | 0.12 | 110 |
| 3. | 28/8 | 2200 | 0.43 | 19.6 | 9.9 | 0.58 | 0.4 | 175 |
| 4. | 29/7 | 2600 | 0.32 | 19.9 | 10.5 | 0.37 | 0.14 | 138 |
| 5. | 30/6 | 2200 | 0.43 | 19.6 | 9.9 | 1.89 | 0.56 | 54 |
| 6. | 30/6[b] | 2600 | 0.18[d] | 21.1 | 11.1 | 0.81 | 0.28 | 35 |

[a] = initial volumetric ratio in extraction cell, phosphate buffer, pH = 7.4, ionic strength = 0.01
[b] = buffer pH = 5.1
[c] = surfactant employed was fluoroether-PEG-fluoroether (7500-1000-7500 MW) triblock
[d] = surfactant employed was twin-tailed fluoroether sulfate (7500 MW tails)
[e] = Sigma 690 total protein kit (TPK)
[f] = subtilisin activity assay based on hydrolysis of N-succinyl Ala-Ala-Pro-Phe p-Nitrianilide
[g] = S/P molar ratio (surfactant molecules per molecule of protein extracted) calculated using amount of protein found via TPK and protein molecular weight of 27,000

EXAMPLE 3

One (1) gram of a nonionic surfactant (fluoroether-PEG-fluoroether, 7500-1000-7500 made as per Example 1, A-2) was dissolved with stirring (magnetic stir bar) in carbon dioxide at 131 bar and 19° C. in the saturation vessel (4) (see FIG. 4); the piston of the syringe pump (15 cc internal volume, 10,000 psi, high pressure equipment) attached to the saturation vessel was completely retracted. A solution of subtilisin Carlsberg (Sigma Chemical Co.) of about 0.8 mg/ml in pH 7 phosphate buffer was prepared and added to entirely fill the extraction vessel (5) (37 ml total). The extraction vessel was equipped with two parallel sapphire windows which allowed viewing of the entire cell contents under pressure. The piston of the syringe pump attached to the extraction vessel (6) was as far forward as possible. Analysis of the initial solution by Lowry protein analysis showed the presence of 0.73 mg/ml. The collection vessel (7) was initially filled with pure carbon dioxide at 19° C. and 131 bar; the back pressure regulator was set just about 131 bar. Simultaneously, the piston of the saturator syringe pump (9) was moved forward while that of the extraction vessel syringe pump (6) was retracted. This led to movement of 8.5 cc of $CO_2$—surfactant solution into the extraction vessel (5), as observed from a linear scale attached to the windows. Both the saturation vessel and Pump 6 were then isolated from the extraction vessel. Given the initial concentration of surfactant in carbon dioxide, it was calculated that 0.2 grams of surfactant were in the extraction vessel; likewise, it was calculated that there were 20.7 milligrams of protein in the 28.5 ml of buffer in the extraction vessel, resulting in a surfactant:protein molar ratio of 17 in the extraction vessel. Prior to stirring, both the upper carbon dioxide phase and lower aqueous phase were transparent, as seen through the windows. The stirring motor was started at 400 rpm and run for 2 to 3 minutes. The motor was then stopped and the contents were allowed to settle for 30 minutes. At this juncture the lower aqueous phase was still transparent while the upper phase was milky white, opaque and visibly more viscous than the original carbon dioxide solution. At this point, the valves leading to the trap (7) were opened and the water pump syringe (6) was moved forward again. As the emulsion phase was pushed into the collection vessel (7), excess carbon dioxide from this vessel exited through the back pressure regulator, while the pressure was maintained at a constant 131 bar. After a significant amount of the emulsion was pushed from the extraction vessel, the valves leading to the collection vessel were closed. The pressure in the collection vessel was slowly released via the back pressure regulator. The amount of water in the collection vessel was too small to measure accurately. The contents of the collection vessel were then washed with a known volume of buffer (same buffer as is used to make up the original protein solution). This solution was tested for protein using the total protein kit and 0.11 mg were found. The extraction vessel was then washed with freon 113 (trichloro, trifluoro ethane), a known solvent for the surfactant. Removal of the solvent from this washing left the surfactant; 0.11 grams were found. Using the molecular weight of the protein (27,000) and the surfactant (16,000) we find a molar ratio of surfactant:protein in the trap of 1690. The activity of the residual protein was found to be negligible using a standard assay (rate of decomposition of the peptide Ala-Ala-Pro-Phe p-Nitroanilide). The specific activity of the initial protein was calculated as the mass of active protein found from the rate assay divided by the mass of total protein shown by the total protein kit; this quantity was also found for the protein in the trap. The percent activity loss was then defined as the initial specific activity minus the final, divided by the initial. For this example, the percent activity loss was 100%, however, further optimization of the process, including increasing the initial protein concentration, adjusting the pH, etc., as described in subsequent examples, resulted in reduced activity retention.

EXAMPLE 4

Following the procedure of Example 3, an anionic (twin-tailed, fluoroether-functional sulfate, molecular weight of 15,000) surfactant made as per Example 1 was used to extract subtilisin Carlsberg (Sigma). The amount of protein in the extraction vessel initially was 24.4 mg; the buffer was a pH 5 acetate mixture. Subsequently, 7.2 ml of carbon dioxide containing 0.17 grams of surfactant were added at 125 bar and 20° C., leading to an initial surfactant:protein ratio of 12. The collection vessel contained 0.18 mg of protein and 0.054 grams of surfactant, giving a molar ratio of surfactant:protein extracted of 518. The specific activity loss was 95%.

EXAMPLE 5

Following the procedure of Example 3, an anionic (twin-tailed, fluoroether-functional sulfate, molecular weight of 15,000) surfactant made as per Example 1 was used to extract subtilisin Carisberg (Sigma). The amount of protein in the extraction vessel initially was 24.2 mg; the buffer was a pH5 acetate mixture. Subsequently, 7.2 ml of carbon dioxide containing 0.2 grams of surfactant were added at 117 bar and 22° C., leading to an initial surfactant:protein ratio of 14. The collection vessel contained 0.16 mg of protein and 0.046 grams of surfactant, giving a molar ratio of surfactant:protein extracted of 486. The specific activity loss was 87%.

EXAMPLE 6

Following the procedure of Example 3, an anionic (twin-tailed, fluoroether-functional sulfate, molecular weight of 15,000) surfactant made as per Example 1 was used to extract subtilisin Carlsberg (Sigma). The amount of protein in the extraction vessel initially was 22.8 mg; the buffer was a pH 5 acetate mixture. Subsequently, 7.2 ml of carbon dioxide containing 0.14 grams of surfactant were added at 125 bar and 20° C., leading to an initial surfactant:protein ratio of 11. The collection vessel contained 0.07 mg of protein and 0.053 grams of surfactant, giving a molar ratio of surfactant:protein extracted of 1242. The specific activity loss was 93%.

EXAMPLE 7

Following the procedure of Example 3, a surfactant mixture was used to extract subtilisin Carlsberg (Sigma). The mixture was 1:1:1 by mass of the anionic surfactant from Example 5, the nonionic surfactant from Example 3 and a fluoroether-functional, dithiocarbamate-copper chelate (made as per Example 1) (molecular weight of 8,000). The amount of protein in the extraction vessel initially was 13 mg; the buffer was a pH 7 phosphate mixture. Subsequently, 7.2 ml of carbon dioxide containing 0.27 grams of surfactant were added at 121 bar and 19° C., leading to an initial surfactant:protein ratio of 35. The collection vessel contained 0.12 mg of protein and 0.034 grams of surfactant, giving a molar ratio of surfactant:protein extracted of 482. The specific activity loss was 62%.

EXAMPLE 8

Following the procedure of Example 3, a surfactant mixture was used to extract subtilisin Carlsberg (Sigma). The mixture was 1:1:1 by mass of the anionic surfactant from Example 5, the nonionic surfactant from Example 3 and a fluoroether-functional, dithiocarbamate-copper chelate (molecular weight of 8,000) made as per Example 1. The amount of protein in the extraction vessel initially was 13 mg; the buffer was a pH 7 phosphate mixture. Subsequently, 7.2 ml of carbon dioxide containing 0.32 grams of surfactant were added at 135 bar and 20° C., leading to an initial surfactant:protein ratio of 42. The collection vessel contained 0.18 mg of protein and 0.023 grams of surfactant, giving a molar ratio of surfactant:protein extracted of 208. The specific activity loss was 24%.

EXAMPLE 9

Following the procedure of Example 3, a surfactant mixture was used to extract subtilisin Carnsberg (Sigma). The mixture was 1:1:1 by mass of the anionic surfactant from Example 5, the nonionic surfactant from Example 3 and a fluoroether-functional, dithiocarbamate-copper chelate (molecular weight of 8,000) made as per Example 1. The amount of protein in the extraction vessel initially was 17 mg; the buffer was a pH 7 phosphate mixture. Subsequently, 6.7 ml of carbon dioxide containing 0.36 grams of surfactant were added at 138 bar and 19° C., leading to an initial surfactant:protein ratio of 35. The collection vessel contained 0.26 mg of protein and 0.087 grams of surfactant, giving a molar ratio of surfactant:protein extracted of 565. The specific activity loss was 58%.

EXAMPLE 10

Following the procedure of Example 3, a surfactant mixture was used to extract subtilisin Carlsberg (Sigma). The mixture was 1:1:1 by mass of the anionic surfactant from Example 5, the nonionic surfactant from Example 3 and a fluoroether-functional, dithiocarbamate-copper chelate (molecular weight of 8,000) made as per Example 1. The amount of protein in the extraction vessel initially was 24 mg; the buffer was a pH 7 phosphate mixture. Subsequently, 6.6 ml of carbon dioxide containing 0.22 grams of surfactant were added at 145 bar and 18° C., leading to an initial surfactant:protein ratio of 19. The collection vessel contained 0.04 mg of protein and 0.055 grams of surfactant, giving a molar ratio of surfactant:protein extracted of 2924. The specific activity loss was 33.5%.

EXAMPLE 11

Following the procedure of Example 3, a surfactant mixture was used to extract subtilisin Carlsberg (Sigma). The mixture was 1:1 by mass of the anionic surfactant from Example 5 and the nonionic surfactant from Example 3. The amount of protein in the extraction vessel initially was 24 mg; the buffer was a pH 5 acetate mixture. Subsequently, 6.6 ml of carbon dioxide containing 0.21 grams of surfactant were added at 124 bar and 20° C., leading to an initial surfactant:protein ratio of 15. The collection vessel contained 0.033 mg of protein and 0.06 grams of surfactant, giving a molar ratio of surfactant:protein extracted of 3069. The specific activity loss was 95%.

EXAMPLE 12

Following the procedure of Example 3, a surfactant mixture was used to extract subtilisin Carlsberg (Sigma). The mixture was 1:1 by mass of the anionic surfactant from Example 5 and the nonionic surfactant from Example 3. The amount of protein in the extraction vessel initially was 23 mg; the buffer was a pH 5 acetate mixture. Subsequently, 6.6 ml of carbon dioxide containing 0.24 grams of surfactant were added at 124 bar and 20° C., leading to an initial surfactant:protein ratio of 18. The collection vessel contained 0.051 mg of protein and 0.03 grams of surfactant, giving a molar ratio of surfactant:protein extracted of 960. The specific activity loss was 92%.

EXAMPLE 13

Following the procedure of Example 3, a surfactant mixture was used to extract subtilisin Carlsberg (Sigma). The mixture was 1:1 by mass of the anionic surfactant from Example 5 and a fluoroether-functional, dithiocarbamate-copper chelate (molecular weight of 8,000) made as per Example 1. The amount of protein in the extraction vessel initially was 16 mg; the buffer was a pH 7 phosphate mixture. Subsequently, 7.7 ml of carbon dioxide containing 0.26 grams of surfactant were added at 131 bar and 20° C., leading to an initial surfactant:protein ratio of 28. The collection vessel contained 0.13 mg of protein and 0.068 grams of surfactant, giving a molar ratio of surfactant:protein extracted of 903. The specific activity loss was 78%.

EXAMPLE 14

Following the procedure of Example 3, a surfactant mixture was used to extract subtilisin Carlsberg (Sigma). The mixture was 1:1 by mass of the anionic surfactant from Example 5 and a fluoroether-functional, dithiocarbamate-copper chelate (molecular weight of 8,000) made as per Example 1. The amount of protein in the extraction vessel initially was 16 mg; the buffer was a pH 7 phosphate mixture. Subsequently, 7.7 ml of carbon dioxide containing 0.3 grams of surfactant were added at 131 bar and 19° C., leading to an initial surfactant:protein ratio of 32. The collection vessel contained 0.32 mg of protein and 0.05 grams of surfactant, giving a molar ratio of surfactant:protein extracted of 268. The specific activity loss was 39%.

EXAMPLE 15

Following the procedure of Example 3, a surfactant mixture was used to extract subtilisin Carlsberg (Sigma). The mixture was 1:1 by mass of the anionic surfactant from Example 5 and a fluoroether-functional, dithiocarbamate-copper chelate (molecular weight of 8,000) made as per Example 1. The amount of protein in the extraction vessel initially was 16 mg; the buffer was a pH 7 phosphate mixture. Subsequently, 7.7 ml of carbon dioxide containing 0.34 grams of surfactant were added at 131 bar and 19° C., leading to an initial surfactant:protein ratio of 37. The collection vessel contained 0.58 mg of protein and 0.059 grams of surfactant, giving a molar ratio of surfactant:protein extracted of 173. The specific activity loss was 58%.

EXAMPLE 16

Following the procedure of Example 3, a surfactant mixture was used to extract subtilisin Carlsberg (Sigma) the mixture was 1:1 by mass of the anionic surfactant from Example 5 and a fluoroether-functional, dithiocarbamate-copper chelate (molecular weight of 8,000) made as per Example 1. The amount of protein in the extraction vessel initially was 18 mg; the buffer was a pH 7 phosphate mixture. Subsequently, 6.4 ml of carbon dioxide containing 0.19 grams of surfactant were added at 138 bar and 19° C., leading to an initial surfactant:protein ratio of 26. The collection vessel contained 0.22 mg of protein and 0.068 grams of surfactant, giving a molar ratio of surfactant:protein extracted of 732. The specific activity loss was 90%.

The experiments described herein demonstrate the feasibility of a $CO_2$ protein extraction process utilizing $CO_2$-soluble surfactants. While the process is not yet optimized as indicated by the wide range of activity loss shown in the examples, applicants have demonstrated the feasibility of the concept. Furthermore, optimization such as that known to those skilled in the art may lead to improved protein activity loss and improved recovery. Without intending to be limited, applicants believe that an increase in initial protein concentration may reduce the activity loss or actually increase the specific activity of the recovered protein. This theory is substantiated by the following examples.

EXAMPLE 17

Following the procedure of Example 3, cell-free unpurified fermentation broth from a fermentation of a mutant subtilisin as described in U.S. Pat. No. 5,204,015 (incorporated herein) was loaded in the extractor at an initial protein concentration of 32.2 mg/ml using total protein method. The extraction was made as per Example 1 at 145 bar and 20° C. The ratio of surfactant to protein in the collection cell was 0.5, the specific activity loss was 10%.

EXAMPLE 18

Following the procedure of Example 3, cell-free broth from a fermentation of a mutant subtilisin as described in U.S. Pat. No. 5,204,015 (incorporated herein) was employed. The extraction was made using a 1:1 by weight mixture of the nonionic surfactant of Example 5 and a fluoroether-functional para-amino phenyl boronic acid (PABA) affinity ligand made as follows. Phenyl amino boronic acid (Aldrich) was added to fluoroether acid chloride (see Example 1) in a 50—50 mixture of Freon 113 and dioxane in the presence of an HCl scavenger (Poly Dmap) to yield the PABA affinity ligand. The extraction was performed at 112 bar and 23° C., the trap contained a surfactant to protein ratio of 0.54, the specific activity loss was 5.3%.

EXAMPLE 19

Following the procedure of Example 3, subtilisin Carlsberg at a concentration in buffer of 3.95 mg/ml (pH=5.3), using fluoroether sulfate at 125 bar and 20° C., was extracted. The extract had a surfactant to protein ratio of 4, the specific activity loss was 14.6%.

EXAMPLE 20

Following the procedure of Example 3, subtilisin Carlsberg at a concentration in buffer of 2.5 mg/ml (pH=6.8), using nonionic surfactant at 123 bar and 21° C., was extracted. The extract had a surfactant to protein ratio of 1.4, the specific activity loss was 14.8%.

EXAMPLE 21

Following the procedure of Example 3, subtilisin Carlsberg at a concentration in buffer of 3.4 mg/ml (pH=8.6), plus a 1:1 mixture of nonionic surfactant of Example 3, and the fluoroether copper chelate made as per Example 1, was extracted at 138 bar and 20° C. The extract had a surfactant to protein ratio of 9 and a specific activity gain of 40%.

EXAMPLE 22

Following the procedure of Example 3, subtilisin Carlsberg at a concentration in buffer of 3.5 mg/ml (pH=8.6), plus 1:1 by weight mixture of nonionic surfactant of Example 3, and fluoroether copper chelate made as per Example 1, was extracted at 138 bar and 20° C. The extract had a surfactant to protein ratio of 8 and a specific activity gain of 19%.

EXAMPLE 23

Following the procedure of Example 3, a comparison was made of two surfactants. An anionic (twin-tailed, fluoroether-functional sulfate, molecular weight of 15,000) surfactant made as per Example 1 and a nonionic surfactant (fluoroether-PEG-fluoroether, 7500-1000-7500 made as per Example 1, A-2) were each used to extract subtilisin Carlsberg (Sigma). The conditions for each extraction were a temperature of 21° C. and a pressure of 150 bar. In the Tables below, $P_i$ is the initial concentration of the subtilisin in the buffer prior to extraction. Table 3 shows the activity retained following depressurization of the emulsion phase. Table 4 shows the extent of solubilization of the subtilisin in the emulsion.

TABLE 3

Specific Activity Retained by Extracted Subtilisin in Liquid $CO_2$

| Surfactant | | | |
|---|---|---|---|
| Ionic Surfactant | | Nonionic Surfactant | |
| Concentration $P_i$ (mg/ml) | Specific Activity (retained %) | Concentration $P_i$ (mg/ml) | Specific Activity (retained %) |
| 0.51 | 0 | 0.31 | 19.3 |
| 0.72 | 7 | 0.41 | 21.4 |
| 0.85 | 13 | 0.44 | 35.5 |
| 1.15 | 52 | 0.7 | 61.1 |
| 1.39 | 61.8 | 1.7 | 67 |
| 1.59 | 73.9 | 3.7 | 76.1 |
| 2.43 | 78.1 | 4.8 | 83.2 |
| 3.9 | 85.4 | | |

TABLE 4

Subtilisin Solubilization in Liquid $CO_2$

| Surfactant | | | |
|---|---|---|---|
| Ionic Surfactant | | Nonionic Surfactant | |
| Concentration $P_i$ (mg/ml) | Protein Solubilized (mg/l) | Concentration $P_i$ (mg/ml) | Protein Solubilized (mg/l) |
| 0.51 | 6 | 0.31 | 5 |
| 0.72 | 8 | 0.41 | 11 |
| 0.85 | 23 | 1.4 | 54 |
| 1.39 | 230 | 1.7 | 53 |
| 1.59 | 342 | 3.7 | 100 |
| 2.43 | 545 | 4.8 | 174 |
| 3.9 | 630 | | |

EXAMPLE 24

Avidin was extracted from buffer using fluoroether-PEG-biotin molecule (bio PEG) using the procedure of Example 3 (column A of Table 5). The bio PEG was made using a method like that of Example 1 A.4, with PEG 600 and a fluorether tail group having a molecular weight of 7500. A different procedure was also performed using the bio PEG surfactant which involves the same apparatus as described below.

The bio PEG affinity surfactant was dissolved in liquid $CO_2$ at 150 bar and 21° C. Avidin solution was pumped inside the extractor while removing the excess $CO_2$ surfactant solution via a back pressure regulator. The mixture was stirred and an emulsion like that shown in FIG. 3, second and third systems (excess buffer at the bottom, a thick, gel-like mass in the middle, and a clear, excess $CO_2$ phase on the top) formed. The emulsion was stripped (at 5 ml/min) with liquid $CO_2$ at 150 bar and 21° C. for 90–120 min, using a back pressure regulator to keep the pressure constant. After every 15–20 min, the $CO_2$ pump was stopped and the mixture stirred. Over time, the size of the gel-like mass (the middle phase) decreased and eventually it disappeared (after 90–120 min). After depressurizing the extractor, the remaining solution was analyzed for the total protein concentration. In Table 5 below, $P_i$ refers to initial avidin concentration in the buffer (pH=7; 0.01 M phosphate), $P_r$ is the concentration of avidin remaining in the buffer after stripping, and the molar ratio, S/P, is the molar ratio of the fluoroether-functional biotin to the avidin.

TABLE 5

Avidin Extracted in Liquid $CO_2$ with Biotin-Based Affinity Ligands

| A | | | B | | |
|---|---|---|---|---|---|
| Bio PEG 600 Kr 7500 | | | Bio PEG 600 Kr 7500 | | |
| $P_i$ (mg/ml) | $P_r$ (mg/ml) | S/P | $P_i$ (mg/ml) | $P_r$ (mg/ml) | S/P |
| 0.55 | 0.34 | 19:1 | 0.55 | 0.19 | 24:1 |
| 0.45 | 0.2 | 47:1 | 0.54 | 0.103 | 115:1 |
| 0.39 | 0.26 | 153:1 | 0.55 | 0.197 | 130:1 |
| | | | 0.67 | 0.25 | 212:1 |

What is claimed is:

1. A surfactant comprising at least two fluoroether $CO_2$-philic tail groups and a head group which interacts with and solubilizes in $CO_2$ a water soluble biomaterial selected from the group consisting of proteins, peptides and amino acids, wherein the surfactant is soluble in $CO_2$ and is selected from the group consisting of fluoroether sulfate, fluoroether-polyethylene glycol block copolymer, fluoroether-functional sorbitol, and fluoroether dithiocarbamate chelate.

2. The surfactant of claim 1, wherein the surfactant is a fluoroether sulfate.

3. The surfactant of claim 1, wherein the surfactant is a fluoroether-polyethylene glycol block copolymer.

4. The surfactant of claim 1, wherein the surfactant is a fluoroether-functional sorbital.

5. The surfactant of claim 1, wherein the surfactant is a fluoroether dithiocarbamate chelate.

6. The surfactant of claim 1, wherein the protein is an enzyme.

7. The surfactant of claim 6, wherein the enzyme is a protease.

8. The surfactant of claim 1 comprising three fluoroether $CO_2$—philic tail groups.

\* \* \* \* \*